(12) United States Patent
Sartor et al.

(10) Patent No.: US 8,729,115 B2
(45) Date of Patent: May 20, 2014

(54) VALSARTAN DERIVATIVES CARRYING NITROGEN OXIDE DONORS FOR THE TREATMENT OF VASCULAR AND METABOLIC DISEASES

(75) Inventors: Dirk Sartor, Rimbach (DE); Armin Scherhag, Dornach (CH)

(73) Assignee: Cardiolynx AG, Basel (CH)

( * ) Notice: Subject to any disclaimer, the term of this patent is extended or adjusted under 35 U.S.C. 154(b) by 4 days.

(21) Appl. No.: 13/641,747

(22) PCT Filed: Apr. 18, 2011

(86) PCT No.: PCT/EP2011/056116
§ 371 (c)(1),
(2), (4) Date: Oct. 17, 2012

(87) PCT Pub. No.: WO2011/131613
PCT Pub. Date: Oct. 27, 2011

(65) Prior Publication Data
US 2013/0041001 A1    Feb. 14, 2013

(30) Foreign Application Priority Data

Apr. 19, 2010  (EP) .................................... 10160289
Apr. 19, 2010  (EP) .................................... 10160292

(51) Int. Cl.
*A01N 43/64*    (2006.01)
*A61K 31/41*    (2006.01)

(52) U.S. Cl.
USPC ......................................................... 514/381

(58) Field of Classification Search
None
See application file for complete search history.

(56) References Cited

U.S. PATENT DOCUMENTS

2011/0230520 A1    9/2011    Sartor et al.

FOREIGN PATENT DOCUMENTS

| WO | 2006/079610 | 8/2006 |
| WO | 2007/019448 | 2/2007 |
| WO | WO 2007019448 A2 * | 2/2007 |

OTHER PUBLICATIONS

CAS RN: 137863-42-4 (entered Dec. 13, 1991).*
CAS RN: 924653-81-6 (entered STN Mar. 4, 2007).*
International Search Report issued Jun. 10, 2011 in International (PCT) Application No. PCT/EP2011/056116, of which the present application is the national stage.
Dirk Sartor et al., U.S. Appl. No. 13/131,722, entitled "Nitrate Derivatives of Cilostazol for the Treatment of Vascular and Metabolic Diseases", filed May 27, 2011.
Dirk Sartor et al., U.S. Appl. No. 13/701,100, entitled "Nitrate and Diazeniumdiolate Derivatives of Pioglitazone", filed Nov. 30, 2012.

* cited by examiner

*Primary Examiner* — Craig Ricci
*Assistant Examiner* — Jared D Barsky
(74) *Attorney, Agent, or Firm* — Wenderoth, Lind & Ponack, L.L.P.

(57) ABSTRACT

Nitrate esters and diazeniumdiolate derivatives of valsartanamide are described. They have valuable properties in the treatment of vascular and metabolic diseases.

10 Claims, 2 Drawing Sheets

VALSARTAN DERIVATIVES CARRYING NITROGEN OXIDE DONORS FOR THE TREATMENT OF VASCULAR AND METABOLIC DISEASES

FIELD OF THE INVENTION

The invention relates to nitrate esters and diazeniumdiolates of valsartanamides useful in the treatment of vascular and metabolic diseases.

BACKGROUND OF THE INVENTION

Vascular and metabolic diseases are, despite cancer, the leading causes of death in the western world. Although many different ways of treating vascular and metabolic diseases are known, there is still a need for improved medication. Lifestyle modifications and drug therapy can decrease and delay the morbidity and mortality associated with these diseases. Treatments which have been proven to reduce the risk for morbidity and mortality in vascular diseases have been typically shown to either improve impaired vascular function or to delay/prevent the progression of vascular dysfunction caused by hypertension, atherosclerosis or other classical metabolic risk factors. Examples for such treatments are calcium channel blockers, beta blockers, angiotension-enzyme converting inhibitors or angiotension receptor blockers.

In patients with coronary artery disease (CAD) due to atherosclerosis, who are suffering from angina pectoris, one of the established standard treatments involves treatment with organic nitrates, specifically nitrate esters, such as glyceryl trinitrate (nitroglycerine), isosorbide dinitrate, or pentaerythrityl tetranitrate, which act all as coronary vasodilators and improve symptoms and exercise tolerance. Most organic nitrates (e.g. mononitrates and trinitrates) are fast acting pharmaceuticals with a relatively short halflife and have the typical disadvantage that patients develop a nitrate tolerance, meaning that part of the pharmacodynamic effect is lost during chronic treatment and a three times daily dosing regimen.

An important group of pharmaceuticals for the treatment of vascular diseases, in particular for patients suffering from hypertension and/or chronic heart failure and concomitant metabolic disease, but not limited to these conditions, are angiotensin II receptor blockers. The antihypertensive activity is due mainly to selective blockade of AT1 receptors and the consequent reduced pressor effect of angiotensin II. Angiotensin II causes potent vasoconstriction, aldosterone secretion and sympathetic activation. All of these actions contribute to the development of hypertension. There are several marketed compounds of this class, in particular losartan, valsartan, olmesartan, irbesartan, candesartan and telmisartan. With the exception of telmisartan, they all comprise a tetrazole structural unit. Several clinical trials have demonstrated that angiotensin II receptor antagonists are as effective as calcium-channel blockers, beta-blockers, and ACE inhibitors in the treatment of hypertension and induce fewer adverse effects. Valsartan is first described in U.S. Pat. No. 5,399,578.

Nitrate esters of drugs in general are described in WO 00/61357. Particular nitrate esters of valsartan derivatives are described in WO 2005/011646 and WO 2007/019448. Diazeniumdiolate derivatives have recently been recognized as alternatives for nitrate esters, setting free two molecules of NO under physiological conditions. A diazenium-diolate derivative of tacrine is described by L. Fang et al., J. Med. Chem. 51, 7666-7669 (2008).

SUMMARY OF THE INVENTION

The invention relates to compounds of formula (IA) or (IB)

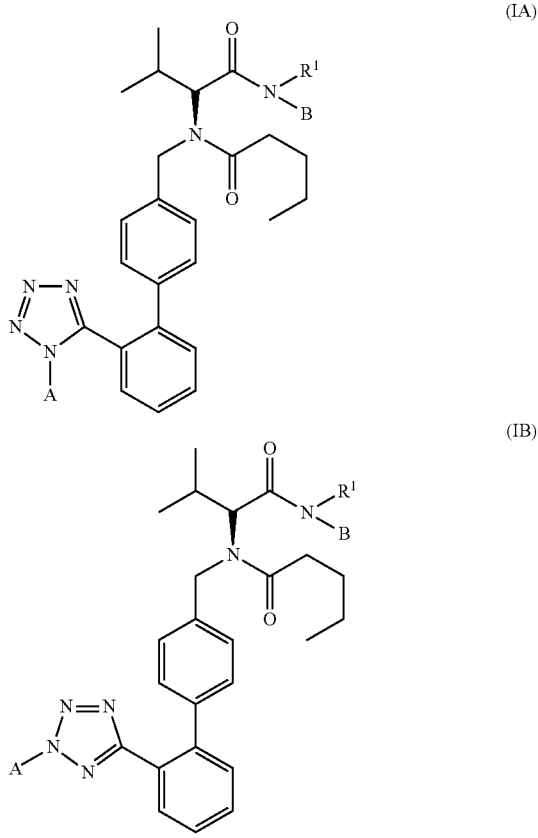

and mixtures thereof, wherein
A is
  —(C=O)$_a$—(CH$_2$)$_b$—O—X;
  —(C=O)$_a$—(CH$_2$)$_c$—CH[(CH$_2$)$_d$—O—X]$_2$;
  —(C=O)—NR$^2$—(CH)$_d$—O—X;
  —CH$_2$—O—(C=O)—NR$^2$—(CH)$_d$—O—X; or
  —CH$_2$—O—(C=O)—O—(CH)$_d$—O—X;
B is
  —(CH$_2$)$_b$—O—X; or
  —(CH$_2$)$_c$—CH[(CH$_2$)$_d$—O—X]$_2$;
X is NO$_2$ or N=(NO)—R$^3$;
R$^1$ is H or C$_1$-C$_4$-alkyl;
R$^2$ is H or C$_1$-C$_4$-alkyl;
R$^3$ is di(C$_1$-C$_{18}$-alkyl)amino, di(2-aminoethyl)amino, N-2-aminoethyl-N-2-hydroxyethyl-amino, pyrrolidino, piperidino, piperazino, 4-(C$_1$-C$_4$-alkyl)piperazino, 4-phenylpiperazino, 4-(2-pyridyl)piperazino or morpholino;
  a is 0 or 1;
  b is between 1 and 18;
  c is 0, 1 or 2; and
  d is between 1 and 6.

Furthermore the invention relates to pharmaceutical compositions comprising the compounds as defined hereinbefore, to the compounds as defined hereinbefore for the treatment of vascular and metabolic diseases, and to a method of treatment of vascular and metabolic diseases using the compounds and pharmaceutical compositions as defined hereinbefore.

The compounds of the invention represent combinations of useful medicaments for the treatment of vascular diseases such as hypertension, angina pectoris (AP), peripheral artery disease (PAD) and cerebrovascular diseases and have valuable properties in the treatment of metabolic diseases such diabetes and dyslipidaemias. The compounds of the invention have superior vasodilating properties compared to valsartan.

DETAILED DESCRIPTION OF THE INVENTION

Figure 1:
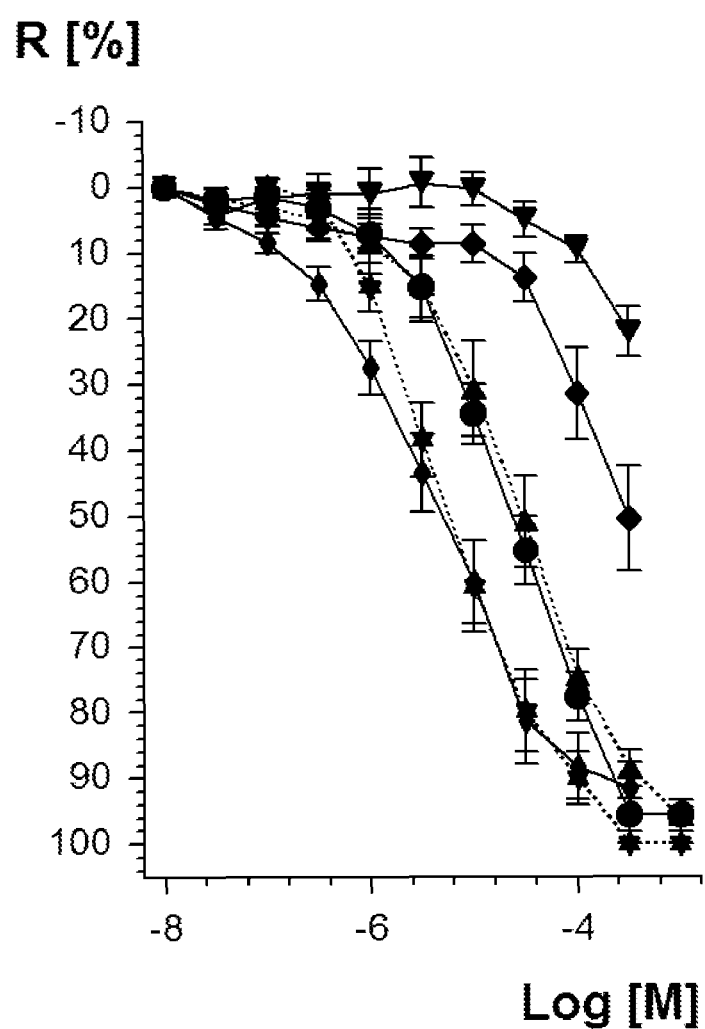
FIG. 1: Isometric tension.
Vasodilation of rat aortic ring segments preconstricted with phenylephrine, Example 3, Table 1. X-axis: relaxation in %; y-axis: log concentration (log M).
Very strong shift to the left from valsartan 3 to valsartan mononitrate 2 to valsartan dinitrate 1, which is as active as isosorbide dinitrate.
● 1-Hydroxy-4-butyl nitrate (HBN), n=8
▲ N-Methyl-N-(4-nitroxybutyl)ammonium nitrate (MNBAN), n=8
▼ Valsartan, compound 3, n=12
◆ Valsartan mononitrate, compound 2, n=12
◆ Valsartan dinitrate, compound 1, n=12
✱ Isosorbide dinitrate (ISDN), n=8
Figure 2:
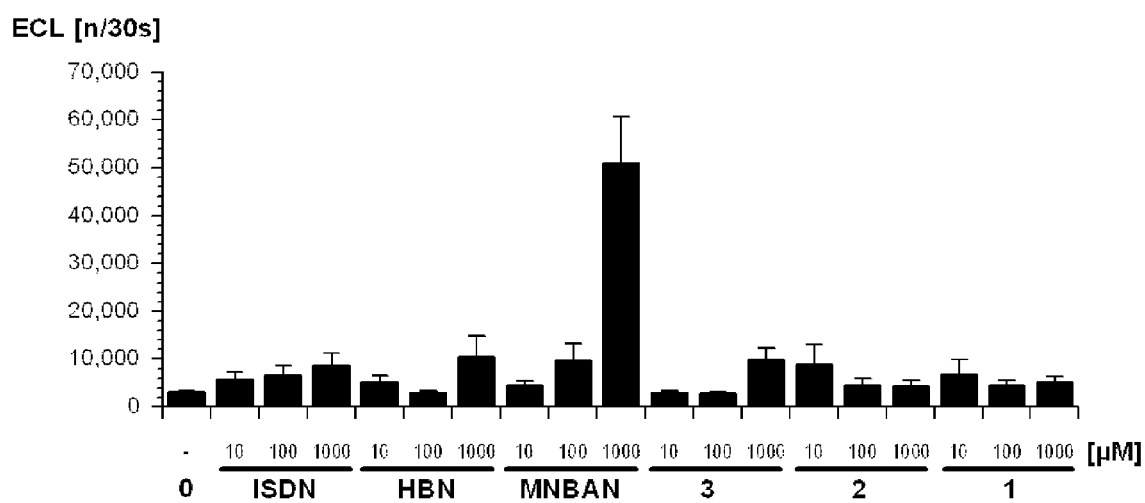
FIG. 2: ROS formation
Reactive oxygen and nitrogen species formation in response to in vitro challenge of isolated rat cardiac mitochondria based on reaction of the chemiluminescence dye L-012 (a luminal analogue), Example 4, Table 2. X-axis: compounds tested with concentration [μM]; y-axis: photons n per 30 sec of emission of chemiluminescence light (ECL).
No ROS formation is observed, even at concentrations of 1000 μM.
HBN: 1-Hydroxy-4-butyl nitrate; MNBAN: N-Methyl-N-(4-nitroxybutyl)ammonium nitrate; compounds 1, 2 and 3, ISDN: Isosorbide dinitrate (ISDN)

The compound of formula (IA) and (IB), wherein A, B and $R^1$ are hydrogen, is known under the name valsartanamide. The corresponding compound wherein A is hydrogen and the amino function $NR^1B$ is replaced by OH is valsartan, compound 3. Compounds of formula (IA) and (IB), wherein A is hydrogen, are tautomers and are in an equilibrium with each other. Compounds of formula (IA) and (IB), wherein A is different from hydrogen, are regioisomers and differ only in the position of the additional substituent in the tetrazole group.
The invention relates to compounds of formula (IA) or (IB) and mixtures thereof, wherein
A is
—$(C=O)_a$—$(CH_2)_b$—O—X;
—$(C=O)_a$—$(CH_2)_c$—CH[$(CH_2)_d$—O—X]$_2$;
—$(C=O)$—$NR^2$—$(CH_2)_d$—O—X;
—$CH_2$—O—$(C=O)$—$NR^2$—$(CH_2)_d$—O—X; or
—$CH_2$—O—$(C=O)$—O—$(CH_2)_d$—O—X;
B is
—$(CH_2)_b$—O—X; or
—$(CH_2)_c$—CH[$(CH_2)_d$—O—X]$_2$;
X is $NO_2$ or N=(NO)—$R^3$;
$R^1$ is H or $C_1$-$C_4$-alkyl;
$R^2$ is H or $C_1$-$C_4$-alkyl;
$R^3$ is di($C_1$-$C_{18}$-alkyl)amino, di(2-aminoethyl)amino, N-2-aminoethyl-N-2-hydroxyethyl-amino, pyrrolidino, piperidino, piperazino, 4-($C_1$-$C_4$-alkyl)piperazino, 4-phenylpiperazino, 4-(2-pyridyl)piperazino, or morpholino;
a is 0 or 1;
b is between 1 and 18;
c is 0, 1 or 2; and
d is between 1 and 6.
$C_1$-$C_{18}$-alkyl is a linear or branched alkyl chain with up to 18 carbon atoms, for example n-octadecyl, n-hexadecyl, n-tetradecyl, n-octyl, isooctyl, n-heptyl, n-hexyl, n-pentyl, or $C_{1-4}$-alkyl, preferably n-hexyl or $C_{1-4}$-alkyl. In di($C_1$-$C_{18}$-alkyl)amino, the $C_1$-$C_{18}$-alkyl residues may be the same or different. For example, di($C_1$-$C_{18}$-alkyl)amino is dimethylamino, diethylamino, N-ethyl-N-methylamino, N-methyl-N-n-octadecylamino, N-n-hexadecyl-N-methylamino, or N-n-hexyl-N-methylamino.
$C_{1-4}$-alkyl is methyl, ethyl, n-propyl, isopropyl, n-butyl, isobutyl, sec-butyl, or tert-butyl, preferably methyl, ethyl or n-propyl, in particular methyl.
The compounds of formula (IA) and (IB), wherein the substituents have the indicated meanings, are useful in the treatment of vascular and metabolic diseases.
Vascular diseases considered are, for example, hypertension and atherosclerosis and typical related consecutive diseases and their related complications, in particular, also ocular and pulmonary hypertension, chronic heart failure, heart failure after a heart attack (myocardial infarction), cerebral ischaemia in general and, specifically, transient ischaemic attacks (TIAs), prolonged neurological deficits (PRIND), stroke (ischaemic and non-ischaemic), chronic cerebrovascular diseases, coronary artery disease, stable and unstable angina pectoris, acute coronary syndrome, acute myocardial infarction, cardiac dysfunction, specifically left or right ventricular dysfunction and hypertrophy, peripheral arterial disease (PAD) at all stages, specifically including abnormalities in micro- and macrovascular function such as neuropathy, endothelial dysfunction, cold feet, impaired wound healing, ischaemic ulcers and necrosis, critical limb ischaemia, and intermittent claudication. Furthermore, treatment and prophylaxis is considered of complications after coronary interventions such as balloon angioplasty and/or stenting, portal hypertension, chronic inflammatory vascular diseases, mixed connective tissue diseases with vascular complications, treatment of vascular complications in patients with Morbus Raynaud or Morbus Osler, treatment of typical micro- and macro vascular complications and resulting disorders, and of vascular and metabolic diseases such as angina pectoris, hypertension and/or diabetes mellitus as described above.
Metabolic disease considered are, for example, the metabolic disorders typically associated with diabetes mellitus type 1 and 2, also including impaired glucose tolerance (pre-diabetes), and specifically all disorders of lipid metabolism such as dyslipidaemias, specifically hypercholesterolaemia, hypertriglyceridaemia, abnormalities of high density lipoproteins alone or in combinations with other dyslipidaemias, abnormalities of Apolipoprotein A1 or other subfractions of lipoproteins, and other metabolic diseases resulting in vascular and metabolic complications and in an increased cardiovascular risk.
Nitrate esters of valsartan have been described previously. It has, however, now be found that a substituent carrying a nitrate ester or a diazenium diolate function can be attached both to the tetrazole structural unit and the amide substituent of valsartanamide, providing easy access to dinitrates, trinitates and tetranitrates, and corresponding diazenium diolates. Valsartan derivatives carrying substituents with nitrate ester or diazenium diolate functions both at the tetrazole unit and the carboxamide functional group release nitrogen monoxide in a sequential manner and have improved properties.
Diazeniumdiolate derivatives of valsartan have not been described previously.

Compounds of formula (IA) and (IB) can be manufactured by methods known in the art. For example, valsartan 3 is first amidated with a primary alkylamine or a secondary N-alkyl-N-methylamine carrying one or two bromine, chlorine or iodine atoms at the optionally branched alkyl group. The obtained valsartanamide, i.e. a compound of formula (IA) and (IB), wherein A is hydrogen, is treated with an acylating compound or an alkylating compound, respectively, further carrying one or two bromine, chlorine or iodine atoms, according to standard procedures well known in the art. In the last step of this synthesis, the bromine, chlorine or iodine atoms are replaced by a nitrate ester or a diazeniumdiolate function by reaction with silver nitrate, or a diazeniumdiolate anion in the presence of strong base in a dipolar aprotic solvent, respectively. Alternatively, valsartan 3 is first amidated with an alkylamine or an N-alkyl-N-methylamine carrying one or two nitrate ester or diazenium diolate functions at the optionally branched alkyl group. The obtained valsartanamide, i.e. a compound of formula (IA) and (IB), wherein A is hydrogen, is treated with an acylating compound or an alkylating compound, respectively, further carrying one or two nitrate ester or diazenium diolate functions. It is also considered to combine these procedures, e.g. using an amidating agent substituted with a nitrate ester (or diazenium diolate) function followed by an alkylating or acylating compound carrying halogen to be replaced by a nitrate ester or a diazenium diolate function in the last step.

Preferred are compounds of formula (IA) or (IB) and mixtures thereof, wherein $R^1$ is methyl or ethyl, or wherein $R^1$ is hydrogen.

Also preferred are compounds of formula (IA) or (IB) and mixtures thereof, wherein X is $NO_2$.

Further preferred are compounds of formula (IA) or (IB) and mixtures thereof, wherein b is between 1 and 6.

More preferred are compounds of formula (IA) or (IB) and mixtures thereof, wherein A is
—(C=O)$_a$—(CH$_2$)$_b$—O—X;
—(C=O)$_a$—(CH$_2$)$_c$—CH[(CH$_2$)$_d$—O—X]$_2$;
—(C=O)—NR$^2$—(CH)$_d$—O—X;
—CH$_2$—O—(C=O)—NR$^2$—(CH)$_d$—O—X; or
—CH$_2$—O—(C=O)—O—(CH)$_d$—O—X;
B is
—(CH$_2$)$_b$—O—X; or
—(CH$_2$)$_c$—CH[(CH$_2$)$_d$—O—X]$_2$;
X is $NO_2$ or N=(NO)—$R^3$;
$R^1$ is methyl or ethyl;
$R^2$ is H, methyl or ethyl;
$R^3$ is diethylamino, pyrrolidino or piperidino;
a is 0;
b is between 1 and 6;
c is 0, 1 or 2; and
d is between 1 and 4.

More preferred are compounds of formula (IA) or (IB) and mixtures thereof, wherein A is
—(C=O)—NR$^2$—(CH)$_d$—O—X;
—CH$_2$—O—(C=O)—NR$^2$—(CH)$_d$—O—X; or
—CH$_2$—O—(C=O)—O—(CH)$_d$—O—X;
B is —(CH$_2$)$_b$—O—X;
X is $NO_2$ or N=(NO)—$R^3$,
$R^1$ is methyl or ethyl;
$R^2$ is H, methyl or ethyl;
$R^3$ is diethylamino, pyrrolidino or piperidino;
b is between 1 and 6; and
d is between 1 and 4;
or such compounds wherein $R^1$ is hydrogen.

Even more preferred are compounds of formula (IA) or (IB) and mixtures thereof, wherein A is
—(C=O)—NR$^2$—(CH)$_d$—O—X;
—CH$_2$—O—(C=O)—NR$^2$—(CH)$_d$—O—X; or
—CH$_2$—O—(C=O)—O—(CH)$_d$—O—X;
B is —(CH$_2$)$_b$—O—X;
X is $NO_2$ or N=(NO)—$R^3$;
$R^1$ is $CH_3$;
$R^2$ is H or $CH_3$;
$R^3$ is pyrrolidino;
b is 2, 3 or 4; and
d is 2, 3 or 4.

Further preferred are compounds of formula (IA) or (IB) and mixtures thereof, wherein A is —CH$_2$—O—(C=O)—NR$^2$—(CH)$_d$—O—X;
B is —(CH$_2$)$_b$—O—X;
X is $NO_2$ or N=(NO)—$R^3$;
$R^1$ is $CH_3$;
$R^2$ is H or $CH_3$;
$R^3$ is pyrrolidino;
b is 2, 3 or 4; and
d is 2, 3 or 4;
or such compounds wherein $R^1$ is hydrogen.

Most preferred are compounds of formula (IA) or (IB) and mixtures thereof, wherein A is —CH$_2$—O—(C=O)—NR$^2$—(CH)$_d$—O—X; B is —(CH$_2$)$_b$—O—X; X is $NO_2$; $R^1$ is H or $CH_3$; $R^2$ is H; b is 4; and d is 2, in particular the compounds of the Examples.

The present invention relates also to pharmaceutical compositions that comprise a compound of formula (IA) or (IB) and mixtures thereof as active ingredient and that can be used especially in the treatment of the diseases mentioned above. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (IA) or (IB) and mixtures thereof and at least one pharmaceutically acceptable carrier.

The invention relates also to pharmaceutical compositions for use in a method for the prophylactic or especially therapeutic management of the human or animal body, in particular in a method of treating a vascular and metabolic disease, especially those mentioned above.

The invention relates also to processes of manufacture and to the use of compounds of formula (IA) or (IB) or mixtures thereof for the preparation of pharmaceutical preparations which comprise compounds of formula (IA) or (IB) or mixtures thereof as active component (active ingredient).

A pharmaceutical composition for the prophylactic or especially therapeutic management of a vascular and metabolic disease, of a warm-blooded animal, especially a human, comprising a novel compound of formula (IA) or (IB) or mixtures thereof as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.001 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a vascular and metabolic disease, which comprises administering a compound of formula (IA) or (IB) or mixtures thereof, wherein the radicals and symbols have the meanings as defined above for formula (IA) or (IB), in a quantity effective against said disease, to a warm-blooded animal requiring such treatment. The compounds of formula (IA) or (IB) or mixtures thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.001 g to approximately 5 g, preferably from approximately 0.25 g to approximately 1.5 g, of a compound of the present invention.

The present invention relates especially also to the use of a compound of formula (IA) or (IB) or mixtures thereof, as such or in the form of a pharmaceutical formulation with at least one pharmaceutically acceptable carrier for the therapeutic and also prophylactic management of a vascular and metabolic disease, in particular of peripheral arterial disease.

The preferred dose quantity, composition, and preparation of pharmaceutical formulations (medicines) which are to be used in each case are described above.

Furthermore, the invention provides a method for the treatment of a metabolic disease, which comprises administering a compound of formula (IA) or (IB) or mixtures thereof, wherein the radicals and symbols have the meanings as defined above, in a quantity effective against said disease, to a warm-blooded animal requiring such treatment.

The following Examples serve to illustrate the invention without limiting the invention in its scope.

Example 1

(2R)-3-Methyl-2-(N-((2'-(1H-tetrazol-5-yl)biphenyl-4-yl)methyl)pentanamido)-butanoyl N-methyl-N-4-nitroxybutyl-amide 2

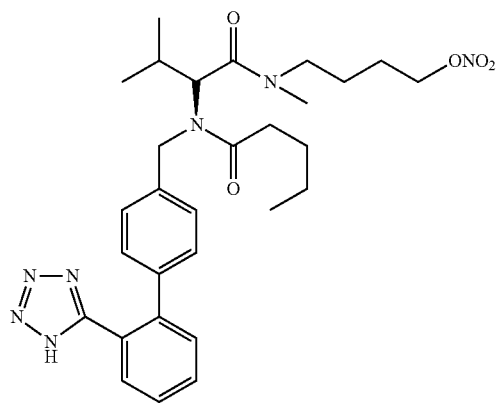

5.0 g Valsartan (3) (11.5 mmol), 4.8 g N-methyl-N-(4-nitroxybutyl)ammonium nitrate (22.7 mmol), 4.6 g diisopropylethylamine (35.5 mmol) and 2.4 g hydroxybenzotriazole (17.7 mmol) are dissolved in 44 g dimethyl formamide (DMF). 3.1 g 1-Ethyl-3-(3-dimethyl-aminopropyl)carbodiimide HCl (EDCI, 16.0 mmol) is added at 0° C., and the mixture stirred for 16 h at room temperature. Water (200 g) and ethyl acetate (120 g) are added, and the organic phase washed with 10% $NaHCO_3$ and citric acid (5 g in 50 g water), then dried over $Na_2SO_4$, and evaporated. The obtained crude oil is purified by chromatography ($SiO_2$; $CH_2Cl_2$:EtOH 96:4), giving 2.60 g (40%) of a waxy solid. $^1$H-NMR (200 MHz, $CDCl_3$): 0.75-0.88 (m, 9H); 1.12-1.38 (m, 2H); 1.47-1.75 (m, 6H); 2.05-2.35 (m, 4H); 2.47 (s, 1.5H); 2.65-3.05 (m, 1H); 3.12 (s, 1.5H); 3.31-3.38 (m, 0.5H); 3.81-3.91 (m, 0.5H); 4.35-4.58 (m, 3H); 5.19-5.38 (m, 1H); 6.81-7.05 (m, 4H); 7.39-7.82 (m, 4H).

The starting material N-methyl-N-(4-nitroxybutyl)ammonium nitrate is obtained as follows: 100 g γ-Butyrolactone (1.16 mol) is added dropwise to 280 g of an aqueous solution of methylamine (40%, 3.61 mol) at 0° C. After 2 h at below 5° C., water and excess starting materials are distilled off. The residue is dissolved in THF and dried over $Na_2SO_4$, then evaporated, dissolved in toluene, and again evaporated. 60 g (0.51 mol) of the obtained crude 4-hydroxy-N-methylbutanamide (131 g, 96%) in 100 g THF is slowly added to 35.2 g $LiAlH_4$ (0.92 mol) in 800 g THF at 0° C. under nitrogen. The mixture is boiled under reflux (54° C.) for 2 h. After cooling to 0° C., aqueous sodium hydroxide (15%) is added and the mixture stirred for 2 h at room temperature. The mixture is filtered, the solids washed with THF, and the combined filtrates evaporated, then dissolved in toluene (175 g) and again evaporated. Distillation at 50° C./6.2 mbar gives 31.5 g (60%) 4-(methylamino)butan-1-ol. $^1$H-NMR (200 MHz, DMSO-$d_6$): 1.40-1.47 (m, 4H); 2.25 (s, 3H); 2.43 (t, J=6.6, 2H); 3.38 (t, J=6.0, 2H).

5 g 4-(Methylamino)butan-1-ol (0.049 mol) is slowly added to 15 g $HNO_3$ (100%, 0.24 mol) at −10° C., care being taken that the temperature does not rise above 10° C. The mixture is stirred for 10 min at 0° C., then poured on ice (15 g) and stirred for 2 h at room temperature. 33 g 2-Butanol is added slowly at 0° C., the obtained mixture (pH 0-1) neutralised (to pH 6) with 15.6 g $NaHCO_3$ at 0° C., filtered and the organic phase dried over $MgSO_4$. 1.2 g Norrit 2× is added, the mixture filtered, and the filtrate evaporated to give 5.4 g (52%) N-methyl-N-(4-nitroxybutyl)ammonium nitrate. $^1$H-NMR (200 MHz, DMSO-$d_6$): 1.56-1.78 (m, 4H); 2.54 (t, J=5.5, 3H); 2.84-2.97 (m, 2H); 4.52 (t, J=5.9, 2H); 8.30 (br. s, 2H).

Example 2

(2R)-3-Methyl-2-(N-((2'-(1-(2"-nitroxyethylaminocarbonyloxymethyl)-1H-tetrazol-5-yl)biphenyl-4-yl)methyl)pentanamido)butanoyl N-methyl-N-4-nitroxybutyl-amide 1A and the corresponding 2-(2"-nitroxyethylaminocarbonyloxymethyl)-2H-tetrazol-5-yl isomer 1B

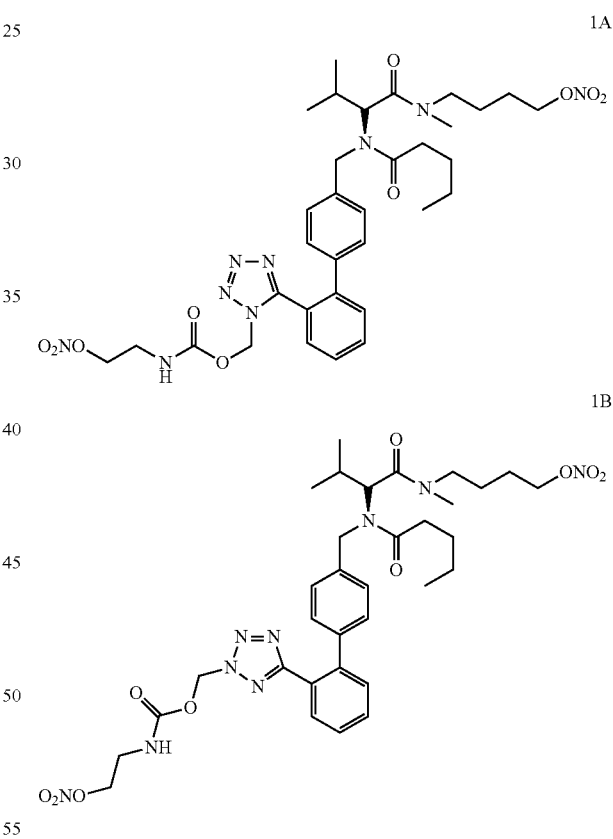

To a solution of 1.70 g valsartan-N-methyl-N-4-nitroxybutyl-amide (2) from Example 1 (3.0 mmol) in 10.2 g DMF were added 0.89 g chloromethyl N-2-nitroxyethylcarbamate (4.5 mmol) and 0.52 g $NEt_3$ (5.1 mmol). The obtained solution was heated to 35° C. and stirred at this temperature for 5 h. After 30 min a turbidity appeared. The reaction mixture was cooled to room temperature and treated with water (60 g) and ethyl acetate (30 g). The obtained organic phase was washed with water, dried over $Na_2SO_4$ and evaporated. The crude product was purified by chromatography ($SiO_2$; $CH_2Cl_2$: MeOH 99:1), which gave 0.88 g (40%) of a colorless oil, a mixture of 1A and 1B.

¹H-NMR 400 MHz, CD₃OD/CDCl₃ 9/1): 1.27-1.58 (m, 4H), 1.40 (s, 3H), 1.41 (s, 3H), 1.72-2.06 (m, 12H), 2.28-2.37 (m, 1H), 2.66-2.71 (m, 2H), 2.84-2.89 (m, 2H), 3.01 (t, J=7.6 Hz, 2H), 3.05 (d, J=6.7 Hz, 2H), 3.71 (dd, J=7.2, 11.8 Hz, 2H), 3.99-4.07 (m, 2H), 4.31-4.40 (m, 1H), 6.78 (dd, J=2.8, 8.7, 1H), 6.82 (d, J=2.8, 1H), 7.23 (d, J=8.7, 1H).

HPLC: Column Symmetry C18, 150×3.0 mm, 3.5 µm; Eluent A 0.5 g ortho-phosphoric acid 85%, 0.75 g KH₂PO₄, 950 mL H₂O and 50 mL CH₃CN; Eluent B CH₃CN; Gradient A:B=60:40 (0 min) to 20:80 (10 min); Flow 1.6 mL/min; Temp. 23° C. The product consists of two components 45:55 with retention time 7.02 and 7.81 min and the expected mass (LC-MS) m/e 728.

The starting material chloromethyl N-2-nitroxyethylcarbamate is obtained as follows: 20 g Ethanolamine (328 mmol) is added dropwise to 60 g HNO₃ (100%) at −20° C., care being taken that the temperature does not rise above 5° C. The mixture is added to ethyl ether (300 g) and stirred for 1 h at 0° C. The obtained suspension is filtered, the solids washed with ethyl ether and dissolved in ethanol (120 g) at 30° C. On cooling to 0° C., the product precipitates again. The solids are added in portions to 60 g HNO₃ (100%) at −5° C., then cooled to −15° C., and treated with ethanol. Ethyl ether (200 g) is added, and the mixture stirred 1 h at −10° C. The obtained suspension is filtered, the solids washed with ethyl ether, and dried in hot air to give 21.9 g (41%) white crystals of 2-nitroxyethyl-ammonium nitrate.

4.25 g Chloromethyl chloroformate (33.0 mmol) are added dropwise in 15 min to 5.0 g 2-nitroxyethylammonium nitrate (29.6 mmol) and 7.5 g triethylamine (74.1 mmol) in 130 g CH₂Cl₂ at −15° C. The mixture is stirred at −10° C. for 1 h. Water (40 g) is added, the phases separated, and the organic phase washed with aqueous citric acid (10%) and saturated aqueous NaHCO₃, then dried over Na₂SO₄, and evaporated to give 4.6 g (78%) of a yellowish oil.

¹H-NMR (200 MHz, CDCl₃): 3.53-3.63 (m, 2H); 4.57 (t, J=5.1, 2H); 5.74 (s, 2H).

Example 3

Vasodilatory Potency of Valsartan Dinitrate (1) and Valsartan Mononitrate (2)

For in vitro characterization of the new valsartan dinitrate and mononitrate compounds of formula 1 and 2, vasodilatory potency was determined by isometric tension studies. According to a published procedure rat aortic ring segments were preconstricted by the alpha-receptor-agonist phenylephrine [Daiber, A. et al., Mol Pharmacol 66 (2004), 1372-1382; Wendt, M. et al., Free Radic Biol Med 39 (2005), 381-391; Munzel, T. et al., J Clin Invest 95 (1995), 187-194]. After reaching a stable preconstriction of vascular tone, the vessels were dose-dependently vasodilated until the final tone at the highest added concentration of the vasodilator was reached. The vasodilators were added at half-logarithmic concentrations starting at $10^{-8}$ M (=10 nanomolar). Vasodilatory potency was compared creating a concentration-relaxation curve. The data are based on experiments with aorta from at least 6 rats on 3 different days. Valsartan dinitrate 1 was as potent as isosorbide dinitrate (ISDN) ($pD_2$-values approximately 5.5). The linkers 1-hydroxy-4-butyl nitrate and N-methyl-N-(4-nitroxybutyl)ammonium nitrate used to introduce the mononitrate functions showed an intermediate vasodilatory potency ($pD_2$-values approximately 4.5). The valsartan mononitrate 2 was significantly less potent in dilating the isolated rat aorta ($pD_2$-value>4). The parent structure valsartan 3 showed weak relaxing effects itself ($pD_2$-value approximately >3). These results demonstrate that dinitrate 1 has a significantly higher vasodilatory potency as compared to mononitrate 2.

TABLE 1

| | Isometric tension (Mean ± SEM) | | | | | |
|---|---|---|---|---|---|---|
| Log [M] | HBN n = 8 | MNBAN n = 8 | 3 n = 12 | 2 n = 12 | 1 n = 12 | ISDN n = 8 |
| −7.5 | 1.84 ± 1.72 | 1.72 ± 1.50 | 4.25 ± 2.13 | 2.45 ± 0.93 | 4.64 ± 0.93 | |
| −7 | 1.42 ± 2.55 | 3.24 ± 2.80 | 1.64 ± 3.06 | 4.61 ± 1.19 | 8.52 ± 1.64 | 0 |
| −6.5 | 3.24 ± 2.77 | 5.04 ± 3.29 | 0.87 ± 2.97 | 6.06 ± 1.69 | 14.66 ± 2.59 | 1.91 ± 2.08 |
| −6 | 7.11 ± 2.87 | 8.33 ± 4.85 | 1.05 ± 3.85 | 7.43 ± 1.86 | 27.39 ± 4.09 | 15.19 ± 3.71 |
| −5.5 | 15.21 ± 4.71 | 14.85 ± 5.75 | −0.58 ± 3.84 | 8.56 ± 2.18 | 43.47 ± 5.88 | 38.41 ± 5.69 |
| −5 | 34.50 ± 4.63 | 30.56 ± 7.29 | 0.29 ± 2.56 | 8.61 ± 2.77 | 59.97 ± 6.28 | 60.69 ± 7.01 |
| −4.5 | 55.15 ± 5.33 | 50.81 ± 6.88 | 4.94 ± 2.65 | 13.69 ± 3.68 | 81.43 ± 6.54 | 79.77 ± 6.35 |
| −4 | 77.74 ± 3.73 | 74.46 ± 4.13 | 9.43 ± 2.03 | 31.38 ± 6.92 | 88.20 ± 5.11 | 89.98 ± 3.97 |
| −3.5 | 95.69 ± 2.40 | 88.56 ± 2.69 | 21.98 ± 3.75 | 50.40 ± 7.89 | 91.52 ± 3.83 | 100 |
| −3 | 95.71 ± 1.27 | 95.84 ± 2.26 | | | | 100 |

HBN: 1-Hydroxy-4-butylnitrate
MNBAN: N-Methyl-N-(4-nitroxybutyl)ammonium nitrate
ISDN: Isosorbide dinitrate Example 4

Lack of Vascular Oxidative Stress Caused by Valsartan Dinitrate (1) and Valsartan Mononitrate (2)

Vascular oxidative stress is a well-known side effect of nitrate tolerance (an adverse condition that develops under chronic nitrate therapy). Therefore, the induction of reactive oxygen and nitrogen species formation in response to in vitro challenges with the test compounds was assessed in isolated mitochondria according to a published procedure [Daiber, A. et al., Mol Pharmacol 66 (2004), 1372-1382; Daiber, A. et al., Biochem Biophys Res Commun 338 (2005), 1865-1874; Daiber, A. et al., Mol Pharmacol 68 (2005), 579-588]. The assay is based on the reaction of the chemiluminescence dye L-012 (a luminol analogue) with reactive oxygen and nitrogen species (RONS, e.g. superoxide anion radicals, peroxynitrite anions or nitrogen dioxide radicals) and subsequent emission of chemiluminescence light (ECL). The signal is counted in photons/time (=counts/30 s). The data are based on experiments with cardiac mitochondria from at least 6 rats on 3 different days. The results demonstrate that isosorbide dinitrate increases the RONS signal in a concentration-dependent fashion, although only slightly. The linkers 1-hydroxy-4-butyl nitrate and N-methyl-N-(4-nitroxybutyl)ammonium nitrate, and valsartan 3 at the highest employed concentration have somewhat more pronounced effects on RONS formation. In contrast, the RONS signal is suppressed at higher concentrations of mononitrate 2 and dinitrate 1. These results demonstrate that valsartan dinitrate 1 does not induce in vitro oxidative stress in isolated mitochondria, in contrast to isosorbide dinitrate or nitroglycerin.

TABLE 2

| ROS formation | | | | |
|---|---|---|---|---|
| Compound | Conc. | Mean | SEM | n |
| Basal | — | 3098.25 | 234.90 | 8 |
| Isosorbide dinitrate | 10 μM | 5718.33 | 1541.18 | 6 |
| | 100 μM | 6608.83 | 2192.78 | 6 |
| | 1000 μM | 8744.83 | 2448.38 | 6 |
| 1-Hydroxy-4-butyl nitrate | 10 μM | 5116.17 | 1460.07 | 6 |
| | 100 μM | 3005.75 | 371.80 | 8 |
| | 1000 μM | 10472.33 | 4340.89 | 6 |
| Methyl-(4-nitroxybutyl)- | 10 μM | 4503.67 | 917.79 | 6 |
| ammonium nitrate | 100 μM | 9667.33 | 3514.27 | 6 |
| | 1000 μM | 51040.00 | 9553.23 | 6 |
| Valsartan 3 | 10 μM | 2971.58 | 444.51 | 12 |
| | 100 μM | 2871.29 | 335.77 | 12 |
| | 1000 μM | 9878.96 | 2332.37 | 12 |
| Valsartan mononitrate 2 | 10 μM | 9007.83 | 3965.67 | 6 |
| | 100 μM | 4532.33 | 1495.71 | 6 |
| | 1000 μM | 4386.00 | 1199.77 | 6 |
| Valsartan dinitrate 1 | 10 μM | 6820.33 | 2984.26 | 6 |
| | 100 μM | 4534.00 | 1068.97 | 6 |
| | 1000 μM | 5088.33 | 1338.29 | 6 |

Example 5

Endothelial Dysfunction, In Vivo Tolerance and Cross-Tolerance Caused by Valsartan Dinitrate 1

To assess the tendency of a given organic nitrate to induce in vivo tolerance and endothelial dysfunction, Wistar rats were treated for 7 days with placebo (solvent alone) or 3 increasing doses of the organic nitrate. Nitrate tolerance and endothelial dysfunction were previously induced by chronic infusion of organic nitrates by osmotic mini pumps (Alzet, Calif., USA) as described [Sydow, K. et al., J Clin Invest 113 (2004), 482-489; Wenzel, P. et al., Arterioscler Thromb Vasc Biol 27 (2007), 1729-1735]. Vascular function was assessed by isometric tension studies as described above. Acetylcholine (ACh) is an endothelium-dependent vasodilator whereas organic nitrates (e.g. compound 1 or nitroglycerin) are endothelium-independent vasodilators. Endothelial dysfunction will result in impaired ACh-dependent relaxation whereas nitrate tolerance and/or vascular dysfunction causes impaired compound 1 dependent or nitroglycerin dependent vasodilation. Results with compound 1 in vivo did not show any significant adverse effects on endothelial or vascular function (impaired Ach response) in terms of induction of in vivo tolerance (impaired compound 1 response) or cross tolerance (ACh, compound 1 and nitroglycerin response) in doses considered of clinical relevance (low and middle dose) and did, up to the highest dose, not show any toxic effects.

Example 6

Effects of Valsartan Dinitrate 1 on Blood Pressure in Beagle Dogs

Valsartan dinitrate 1 was administered to Beagle dogs. Three groups of two dogs each were administered valsartan dinitrate 1 using three different formulations. Each group was administered three ascending doses separated by 4 wash out days providing 9 different treatments as shown in the following table:

TABLE 3

| Administration scheme in Beagle dogs | | | |
|---|---|---|---|
| | Dose | | |
| Formulation | Dose 1 | Dose 2 | Dose 3 |
| Group 1 Valsartan dinitrate 1 in Solutol (gavage) | 5 mg/kg | 15 mg/kg | 45 mg/kg |
| Group 2 Valsartan dinitrate 1 in capsule (oral) | 5 mg/kg | 15 mg/kg | 45 mg/kg |
| Group 3 Valsartan dinitrate 1 in Solutol (intravenous) | 1 mg/kg | 5 mg/kg | 15 mg/kg |

Group 1 was administered valsartan dinitrate 1 solubilized in a solution consisting of 30% Solutol (nonionic solubilizer and emulsifying agent produced from ethylene oxide and 12-hydroxystearic acid, available from BASF). The liquid was administered per gavage. Group 2 was administered valsartan dinitrate 1 non formulated filled into gelatine capsules. The capsule was administered orally.

Group 3 was administered the same solution of valsartan dinitrate 1 in 30% Solutol as used in group 1. In this group the liquid was administered intravenously as a slow bolus injection.

Blood pressure was assessed for all treatments before dosing and 1, 2, 3, 4, 5, 6, 8, 12 and 24 h after dosing.

A blood pressure lowering effect, derived from the NO donating portion of the molecule or from the valsartan portion of the molecule or both, was observed. Animals of groups 2 and 3 showed two sequential lowerings of blood pressure, consistent with an initial lowering caused by the NO-donating part of the molecule, followed by the standard blood pressure lowering as known from valsartan 3. Overall the results indicate that valsartan dinitrate 1 has an effect on blood pressure lasting at least 10 hours, showing a profile consistent with both its NO-donating function as well as its valsartan moiety. For several animals the blood pressure lowering is observed up to 24 hours.

The invention claimed is:
1. A compound of formula (IA) or (IB)

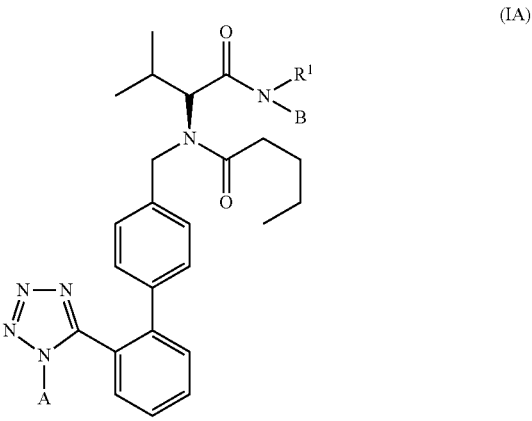

(IA)

-continued (IB)

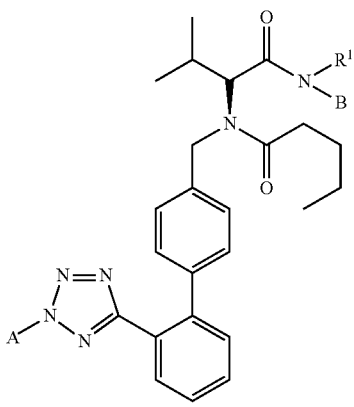

or a mixture thereof, wherein
A is
—(C=O)—NR²—(CH)$_d$—O—X;
—CH₂—O—(C=O)—NR²—(CH)$_d$—O—X; or
—CH₂—O—(C=O)—O—(CH)$_d$—O—X;
B is —(CH₂)$_b$—O—X;
X is NO₂ or N=(NO)—R³;
R¹ is methyl or ethyl;
R² is H, methyl or ethyl;
R³ is diethylamino, pyrrolidino or piperidino;
b is between 1 and 6; and
d is between 1 and 4.

2. The compound according to claim 1 of formula (IA) or (IB) or a mixture thereof, wherein X is NO₂.

3. The compound according to claim 1 of formula (IA) or (IB) or a mixture thereof, wherein
A is
—(C=O)—NR²—(CH)$_d$—O—X;
—CH₂—O—(C=O)—NR²—(CH)$_d$—O—X; or
—CH₂—O—(C=O)—O—(CH)$_d$—O—X;
B is —(CH₂)$_b$—O—X;
X is NO₂ or N=(NO)—R³;
R¹ is CH₃;
R² is H or CH₃;
R³ is pyrrolidino;
b is 2, 3 or 4; and
d is 2, 3 or 4.

4. The compound according to claim 1 of formula (IA) or (IB) or a mixture thereof, wherein
A is —CH₂—O—(C=O)—NR²—(CH)$_d$—O—X;
B is —(CH₂)$_b$—O—X;
X is NO₂ or N=(NO)—R³;
R¹ is CH₃;
R² is H or CH₃;
R³ is pyrrolidino;
b is 2, 3 or 4; and
d is 2, 3 or 4.

5. The compound according to claim 1 of formula (IA) or (IB) or a mixture thereof, wherein
A is —CH₂—O—(C=O)—NR₂—(CH)$_d$—O—X;
B is —(CH₂)$_b$—O—X; X is NO₂;
R1 is CH₃;
R₂ is H;
b is 4; and
d is 2.

6. The compound (2R)-3-methyl-2-(N-((2'-(1-(2"-nitroxyethylaminocarbonyloxymethyl)-1H-tetrazol-5-yl)-biphenyl-4-yl)methyl)pentanamido)butanoyl N-methyl-N-4-nitroxybutyl-amide, (2R)-3-methyl-2-(N-((2'-(2-(2"-nitroxyethylaminocarbonyloxymethyl)-2H-tetrazol-5-yl)-biphenyl-4-yl)methyl)pentanamido)butanoyl N-methyl-N-4-nitroxybutyl-amide, or a mixture thereof, according to claim 1.

7. The compound (2R)-3-methyl-2-(N-((2'-(1-(2"-nitroxyethylaminocarbonyloxymethyl)-1H-tetrazol-5-yl)biphenyl-4-yl)methyl)pentanamido)butanoyl N-methyl-N-4-nitroxybutyl-amide, according to claim 6.

8. The compound (2R)-3-methyl-2-(N-((2'-(2-(2"-nitroxyethylaminocarbonyloxymethyl) -2H-tetrazol-5-yl)biphenyl-4-yl)methyl) pentanamido)butanoyl N-methyl-N-4-nitroxybutyl-amide, according to claim 6.

9. The mixture of compounds (2R)-3-methyl-2-(N-((2'-(1-(2"-nitroxyethylaminocarbonyloxymethyl)-1H-tetrazol-5-yl)biphenyl-4-yl)methyl)pentanamido)butanoyl N-methyl-N-4-nitroxybutyl-amide and (2R)-3-methyl-2-(N-((2'-(2-(2"-nitroxyethylaminocarbonyloxymethyl)-2H-tetrazol-5-yl)biphenyl-4-yl)methyl)pentanamido)butanoyl N-methyl-N-4-nitroxybutyl-amide, according to claim 6.

10. A pharmaceutical composition comprising a compound according to claim 1.

* * * * *